(12) United States Patent
Staveski et al.

(10) Patent No.: US 7,186,725 B2
(45) Date of Patent: Mar. 6, 2007

(54) ANTI-INFLAMMATORY COMPOSITIONS AND METHODS

(75) Inventors: Mark M. Staveski, Taunton, MA (US); Robert J. Miller, E. Bridgewater, MA (US); Sharon R. Nahill, Belmont, MA (US)

(73) Assignee: Genzyme Corporation, Cambridge, MA (US)

( * ) Notice: Subject to any disclaimer, the term of this patent is extended or adjusted under 35 U.S.C. 154(b) by 192 days.

(21) Appl. No.: 10/746,034

(22) Filed: Dec. 23, 2003

(65) Prior Publication Data

US 2004/0180871 A1    Sep. 16, 2004

Related U.S. Application Data

(60) Provisional application No. 60/437,954, filed on Jan. 3, 2003.

(51) Int. Cl.
   *A61K 31/497* (2006.01)
   *A61K 31/445* (2006.01)
   *C07D 239/02* (2006.01)
   *C07D 211/56* (2006.01)

(52) U.S. Cl. ............. 514/254.01; 514/326; 514/256; 544/333; 544/335; 546/210

(58) Field of Classification Search ........... 514/254.01, 514/326, 256; 544/333, 335; 546/210
See application file for complete search history.

(56) References Cited

U.S. PATENT DOCUMENTS

| | | | |
|---|---|---|---|
| 3,061,640 A | 10/1962 | Beaver et al. |
| 4,293,549 A | 10/1981 | Rachlin et al. |
| 4,597,902 A | 7/1986 | Shanklin, Jr. et al. |
| 4,937,270 A | 6/1990 | Hamilton et al. |
| 5,057,503 A | 10/1991 | Czop et al. |
| 5,356,883 A | 10/1994 | Kuo et al. |
| 5,506,151 A | 4/1996 | Ito et al. |
| 5,527,893 A | 6/1996 | Burns et al. |
| 5,679,654 A | 10/1997 | Tzianabos et al. |
| 5,700,787 A | 12/1997 | Tzianabos et al. |
| 5,760,200 A | 6/1998 | Miller et al. |
| 5,817,643 A | 10/1998 | Jamas et al. |
| 5,849,794 A | 12/1998 | Bianchi et al. |
| 6,211,549 B1 | 4/2001 | Funaki et al. |

FOREIGN PATENT DOCUMENTS

| | | | |
|---|---|---|---|
| DE | 2847792 | * | 5/1979 |
| EP | 0667529 | | 8/1995 |
| EP | 0731099 A1 | | 9/1996 |
| GB | 1112034 | | 5/1968 |
| JP | 5192865 | | 0/1978 |
| WO | WO92/00105 | | 9/1992 |
| WO | WO92/20349 | | 11/1992 |
| WO | WO95/09619 | | 4/1995 |
| WO | WO99/06354 | | 2/1999 |
| WO | WO99/32463 | | 7/1999 |
| WO | WO00/35449 | | 6/2000 |
| WO | WO00/59490 A2 | | 10/2000 |
| WO | WO00/59490 A3 | | 10/2000 |
| WO | WO 01/19725 | * | 3/2001 |
| WO | WO 01/30781 | * | 5/2001 |
| WO | WO 01/47922 | * | 7/2001 |
| WO | WO 01/57008 | * | 8/2001 |
| WO | WO02/059081 | | 8/2002 |

OTHER PUBLICATIONS

Santha et al., "Radioprotective Effect of New Xanthogenic-Acid Derivatives on Mice Exposed to Mixed Reactor Radiation" *RK Press V.* 1972, No. RECD 1973, pp. 843-845 (1973).
Legheand, J. et al., "Synthesis and in vitro pharmacological study of acetylcholine amide analogs", *Eur. J. Med. Chem—Chim. Ther.*, V. 9, No. 2, pp. 193-196 (1974) (with English summary, pp. 195-196).
Barlow et al., "The effects of replacing ester by amide on the biological properties of compounds related to acetylcholine", *Br. J. Pharmacol.*, V. 62, No. 1, pp. 39-50 (1978).
Beuvery et al., "Analytical, Toxicological and Immunological Consequences of the Use of N-Ethyl-$N^1$-(3-Dimethylaminopropyl) Carbodiimide as Coupling Reagent for the Preparation of Meningococcal Group C Polysaccharide-Tetanus Toxoid Conjugate as Vaccine For Human Use", *IABS/WHO/UCSF Symposium on the Use and Standardization of Chemically Defined Antigens*, San Francisco, USA, *Develop. biol. Standard.* V. 63, pp. 117-128 (1986).
Kuo et al., "Chemical Modification of Hyaluronic Acid by Carbodiimides", *Bioconjugate Chem*, V. 2, pp. 232-241 (1991).
Onderdonk, et al., "Anti-Infective Effect of Poly-β-6-Glucotriosyl-β1-3-Glucopyranose Glucan in Vivo", *Infection and Immunity*, V. 60, No. 4, pp. 1642-1647 (1992).
Hogaboam, et al., "An orally active non-selective endothelin receptor antagonist, bosentan, markedly reduces injury in a rat model of colitis", *Eur. J. Pharma*, V. 309, pp. 261-269 (1995).
Tzianabos et al., "Polysaccharide-mediated Protection Against Abscess Formation in Experimental Intra-Abdominal Sepsis", *Journal of Clinical Investigation*, V. 96, No. 6, pp. 2727-2731 (1995).
Tzianabos et al., "Protection against Experimental Intraabdominal Sepsis by Two Polysaccharide Immunomodulators", *Journal of Infectious Diseases*, v. 178, pp. 200-206 (1998).

(Continued)

Primary Examiner—D. Margaret Seaman
(74) Attorney, Agent, or Firm—Isabelle A. S. Blundell

(57) ABSTRACT

The present invention provides compositions and their use in the treatment of inflammatory diseases caused by T-cell proliferation such as sepsis, inflammatory bowel diseases, autoimmune encephalomyelitis, or lupus. The compositions comprise disubstituted ureas of Formulas I, II, III or IV:

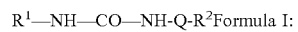

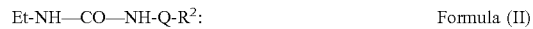

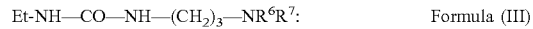

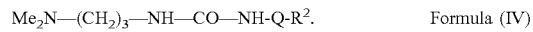

10 Claims, 2 Drawing Sheets

OTHER PUBLICATIONS

W. I. Weaver, et al., "Morpholinomethyl Derivatives of Urea and Substituted Urea", *J. Amer. Chem. Soc.*, vol. 66, No. 2 (1944) pp. 222-225.

F. Perini et al., "Conversion of Ureidomalonates and 5-Carbalkoxyhydantoins into 5-Ureido-4, 6-pyrimidinediones", *The Journal of Organic Chemistry*, vol. 35, No. 3 (1970) pp. 222-225.

G. Crank et al., "Derivatives of 2-Aminooxazoles Showing Antinflammatory Activity", *Journal of Medicinal Chemistry*, vol. 14, No. 11 (1971) pp. 1075-1077.

A. Shafiee et al., "Synthesis and Pharmacological activity of Benzo[*b*]thiophene-3-carboxylic Acid Derivatives", *J. Pharm. Sci.*, vol. 72, No. 2 (1983) pp. 198-202.

M. Fujita et al., "Synthesis and Bioactivities of Novel Bicyclic Thiophenes and 4,5,6,7-Tetrahydrothieno [2,3-c]pyridines as Inhibitors of Tumor Necrosis Factor-α (TNF-α) Production", *BIoorganic & Medicinal Chemistry Letters*, vol. 12 (2002) pp. 1897-1900.

R. P. Alexander et al., "cdp840. a Prototype of a Novel Class of Orally Active Anti-inflammatory Phosphodiestrease 4 Inhibitors", *Bioorganic & Medicinal Chemistry Letters* vol. 12 (2002) pp. 1451-1456.

B. Ruiz-Perez et al., "Protection against Lethal Intra-abdominal Sepsis by 1-(3-dimethylaminopropyl)-3-ethylurea", *Journal of Infectious Diseases*, vol. 188, No. 3 (2003) pp. 378-387.

Y. Kasai et al., "Spectrophotometric determination of basic carbodiimide perchlorates by the use of ferric benzohydroxamate formation", *Chemical & Pharmaceutical Bulletin*, vol. 33, No. 12 (1085) pp. 5375-9 Database Online CA, (abstract).

Database, Crossfire, Beilstein Online, Beilstein Registry No. 5223366, 5205423, 2833563, Ibrahim et al., *J. Chem. Soc. Perkin Trans* 2, EN; (1982) pp. 1459-1466 (abstract).

Database Crossfire, Beilstein Online, Reaction ID 688546, Selleri et al., *Farmaco Ed. Sci.*, 12, (1057) pp. 3-11 (abstract).

Database Crossfire, Beilstein Online, Reaction ID 1290602. Sheehan et al., *J Org. Chem*; EN; 26; (1961); pp. 2525-2528 (abstract).

Database Crossfire, Beilstein Online, Beilstein Registry No. 2655850, CHITI, *Farmaco Ed. Sci.*, 15 (1960) pp. 114-122 (abstract).

Database Crossfire, Beilstein Online, Reaction ID 9203927, Ryczek, *J. Heterocycl. Chem*; EN; 39;5 (2002) pp. 997-1000 (abstract).

Database Crossfire, Beilstein Online, Beilstein Registry No. 8064736, FABIS, et al., *Tetrahedron*, vol. 54, No. 36 (1998) pp. 10789-10800 (abstract).

Database Crossfire, Beilstein Online, Beilstein Registry No. 1222050, Hong et al., *J. Med. Chem.*, 16 (1973) p. 139 (abstract).

Database Crossfire, Beilstein Online, Reaction ID 9084756, Mock, et al., *J. Chem. Soc. Perkin Trans* 2, 4 (2002) pp. 843-847 (abstract).

Database Crossfire, Beilstein Online, Reaction ID32297, Dickshoorn, *Recl. Trav. Chim. Pays-Bas*, 48, (1929) p. 552 (abstract).

Database Crossfire, Beistein Online, Beilstein Registry No. 2101728, Chimija, 57, (1962/63) pp. 105-107 (abstract).

Database Crossfire, Beilstein Online, Reaction ID 630163, Cahours, et al., *Chem.*, 102, 1857, p. 296 (abstract).

Database Crossfire, Beilstein Online, Beilstein Registry No. 392384, Gostea et al., *Rev. Chim*, 22 (1971) p. 711 (abstract).

Database Crossfire, Beilstein Online, Beilstein Registry No. 395838, Novikov, *Chem. Heterolcycl. Compd* (Eng. Transl.); 4 (1968) p. 89 (abstract).

Database Crossfire, Beilstein Online, Beilstein Registry No. 2117402, Borgna et al., *Farbaco Ed. Sci.*, 33 (1978) pp. 510-513 (abstact).

Database Crossfire, Beilstein Online, Reaction ID 1404062, Rudchenko et al., *Bull. Russ. Acad. Sci. Dic. Chem. Sci* (Engl. Trans) vol. 42, No. 10.2 (1992) pp. 1920-1921 (abstract).

Database Crossfire, Beilstein Online, Beilstein Registry No. 2432164, Saavedra et al., *Org. Prep. Proced. Int.*, vol. 24, No. 6 (1992) pp. 655-660 (abstract).

Database Crossfire, Beilstein Online, Beilstein Registry No. 218168, Hof et al., *Arzneim. Forsch.*, vol. 37, No. 3 (1987) pp. 306-309 (abstract).

* cited by examiner

ANTI-INFLAMMATORY COMPOSITIONS AND METHODS

This application claims priority from U.S. provisional application No. 60/437,954 filed on Jan. 3, 2003.

DESCRIPTION OF INVENTION

1. Field of the Invention

This invention relates to compositions and methods of modulating an inflammatory or immune response.

2. Background of Invention

In WO00/59490, Ethyl dimethylaminopropylurea (1) (EDU) has been shown to be effective in preventing sepsis and its mode of action has been linked to the inhibition of Concanavalin A activated T-cell proliferation.

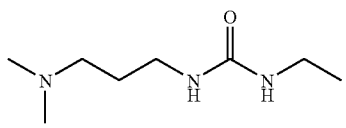

SUMMARY OF THE INVENTION

Therefore, a series of analogs of EDU (see formula I described below) have now been prepared and shown to be active agents against a modified Concanavalin A activated T-cell proliferation assay using purified rat T cells. Compounds from this series showed in-vivo activity in a rat model of inflammatory bowel disease (IBD), a mouse model of septic shock, and a mouse model of autoimmune encephalomyelitis (EAE). This in-vivo activity coupled with lack of cellular toxicity and in-vivo toxicity demonstrate that these types of compounds can be used as anti-inflammatory agents in immune responses. T-cell proliferation is an immune response indicative of inflammatory processes such as those found in IBD, EAE, sepsis, rheumatoid arthritis and lupus. Therefore, compounds of the present invention are useful in the treatment or management of inflammatory responses or diseases such as treatment of sepsis, IBD, EAE, and lupus for example.

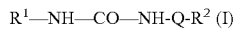

or a pharmaceutically acceptable salt thereof, wherein $R^1$ is a lower C2–C5 alkyl group, straight or branched chain and optionally substituted by an amino group of formula —$NR^3R^4$, wherein $R^3$ and $R^4$ are independently H, or C1–C3 alkyl group;

Q is either a bond or a divalent C1–C5 straight or branched alkyl or alkenyl group;

$R^2$ is either one or more of the following groups a. H, adamantyl, —OH provided that $R^2$ is not a bond,
b. $OR^5$, —$COR^5$, —$CO_2R^5$ wherein $R^5$ is a C1–C4 straight or branched alkyl group,
c. C6–C10 aryl group,
d. C5–C10 heteroaryl group wherein one or more ring positions may be occupied by N, S, or O,
e. C5–C10 heterocyclic group wherein one or more ring positions may be occupied by N, S, or O, wherein the aryl, heteroaryl, or heterocyclic ring is unsubstituted or substituted by one or more of the following groups
   i. $R^5$, —CN, Halogen, $OR^5$, —$COR^5$, —$CO_2R^5$, $OCF_3$, —$CONH_2$, —$SO_2NH_2$, and $NO_2$, wherein $R^5$ is a C1–C4 straight or branched alkyl group, and
f. $NR^6R^7$, wherein $R^6$ and $R^7$ are
   i. independently a C1–C5 straight or branched alkyl or unsubstituted or substituted by —OH or cyclopropyl, phenyl
   ii. together with the N forming a 5-or 6-membered monocyclic ring having one or more ring positions occupied by another N, S, or O, wherein the heteroaryl ring thus formed is unsubstituted or substituted by one or more of the following groups
      1. $R^5$, —CN, halogen, $OR^5$, —$COR^5$, —$CO_2R^5$, $OCF_3$, —$CONH_2$, —$SO_2NH_2$, wherein $R^5$ is a C1–C4 straight or branched alkyl group,
      2. C1–C5 alkyl or alkylene group substituted by an aryl group, and
      3. C6 or C10 aryl or heteroaryl group unsubstituted or substituted by one ore more of $R^5$ as defined above, $CF_3$, and halogen, wherein the aryl or hetero aryl may be a pending group off one position of, or a fused with, the $NR^6R^7$ ring.

DETAILED DESCRIPTION OF INVENTION

Figure 1:
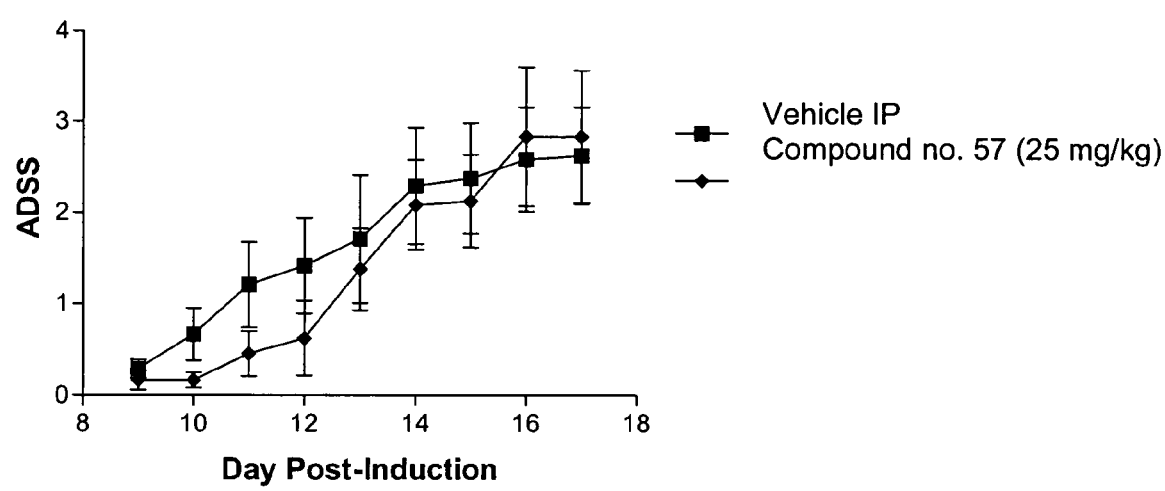
FIG. 1 is a plot of the assessment of the disease severity score (ADSS) over time post challenge in a mouse model of EAE for control (vehicle) and treated with a compound of the invention.

Compounds of Formula I (above), based on an ethyl dimethylaminopropylurea (1) parent structure, have been discovered as active agents against a modified Concanavalin A activated T-cell proliferation assay using purified rat T-cells. These cells were incubated for 4 days and pulsed with [$^3$H] thymidine for the last 16 hrs of incubation. [$^3$H] Thymidine uptake was measured as the mean counts per minute (cpm) of duplicate experimental cultures. The compounds of the present invention were discovered by screening a compound library. (directed analogs of parent compound 1) using an assay designed to identify inhibitors of Concanavalin A stimulated T-cell proliferation. Normal dermal fibroblasts and kidney epithelial cell toxicity assays were run on active compounds to eliminate non-selective cytotoxic compounds.

Compounds comprising the present invention are listed in the following tables along with their respective screening data. It was found that the bioactivity of the urea is mainly improved when substituents are introduced. The scope of these substitutions, which include substitutions to either the ethyl or dimethylaminomethyl portion of the compound 1, is illustrated in Tables 1–3. Table 4 lists salt forms that were made from selected analogs. While the T-cell proliferation assay is commonly used for assessing T-cell response, it reveals little about the functional capabilities of the T-cells that respond to it. These must be determined by running functional assays. Towards this end, a selected compound was evaluated against a panel of cytokines and is summarized in Table 5.

More specifically, preferred embodiments of formula I include compounds of formula II, formula II and formula IV and pharmaceutically acceptable salts thereof as set out below:

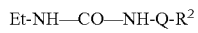    Formula (II):

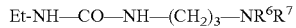    Formula (III):

    Formula (IV):

Wherein Q, $R^2$, and $NR^6R^7$ are as defined above.

In $R^1$ of formula I above, illustrative examples of a C2–C5 alkyl include, but are not limited to, ethyl, propyl, isopropyl, butyl, 2-butyl, pentyl, 2-pentyl, 3-pentyl, and terbutyl. A C1–C3 alkyl group includes methyl, ethyl, propyl, and isopropyl. Thus, illustrative examples of $NR^3R^4$, include amino, methyl amino, dimethyl amino, ethyl amino, dimethyl amino, ethyl, methyl amino, propylamino, methylpropylamino, ethylpropylamino, dipropylamino, isopropylamino, methylisopropyl amino, ethylisopropyl amino, and diisopropylamino. Preferred $R^1$ groups include ethyl and dimethylaminopropyl group.

In Q of formulas I, II and IV above, illustrative examples of a C2–C5 straight or branched alkyl include, but are not limited to, ethyl, propyl, isopropyl, butyl, 2-butyl, pentyl, 2-pentyl, 3-pentyl, and terbutyl; and illustrative examples of a C2–C5 straight or branched alkenyl include, but are not limited to, ethylene, propylene, propyl-2-ene, isopropylene, butyl-1-ene, butyl-2-ene, butyl-3-ene, 2-methyl-propyl-2-ene, 2-methylpropy-1-ene, butadiene, pentyl-1-ene, pentyl-2-ene, pentyl-3-ene, pentyl-4-ene, 2-methylbutadiene, 3-methylbutadiene, 1,3-pentadiene, 2,4-pentadiene. Divalence positions on these groups may be obtained by the removal of two hydrogen atoms from any carbon positions including the following combinations whenever applicable to the alkyl or alkylene group (C1,C1), (C1,C2), (C1,C3), (C1,C4), (C1,C5), (C2,C2), (C2,C3), (C2,C4),(C2,C5), (C3, C3), (C3,C4), (C3,C5), (C4,C4), (C4,C5), and (C5, C5). Preferred examples for Q includes in addition to a bond, the following groups: —CH$_2$—, —(CH$_2$)$_2$—, —(CH$_2$)$_3$—, —(CH$_2$)$_4$—, —C(CH$_2$)$_2$—CH$_2$—, —CH$_2$—C(CH$_3$)$_2$—CH$_2$—, and —CH$_2$—CH=CH—.

In $R^2$ of formulas I, II and IV above, illustrative examples of a C2–C4 straight or branched alkyl include, but are not limited to, ethyl, propyl, isopropyl, butyl, and 2-butyl; illustrative example of a C6–C10 aryl group include, but are not limited to, phenyl, 1-naphthyl, 2-naphtlyl; illustrative examples of C5–C10 heterocyclic rings include, but are not limited to, piperidyl, pyrrolidyl, piperazyl, morpholine, tetahydrofuranyl, dioxanyl; illustrative examples of heteroaryl group include, but are not limited to, furanyl, thiophenyl, pyrrolyl, pyrazolyl, imidazolyl, triazolyl, dithiolyl, oxathiolyl, isoxazolyl, oxazolyl, thiazolyl, pyridinyl, piridazinyl, pyrimidinyl, pyrazinyl, , benzofuranyl, benzothiophenyl, indolyl, quinolinyl, isoquinolinyl, benzothiazoyl, benzimidazolyl, benzoxazinyl, benzothiadiazolyl, naphthyridinyl, pyrido[3,4-b]pyridinyl, pyrido[3,2-b]pyridinyl, pyrido[4,3-b]pyridinyl, and 4-aminopyrazolo[3,4-d]pyrimidinyl.

Preferred embodiments for $R^2$ include but are not limited to, 2-toluyl, 3-toluyl, 4-toluyl, 2,3-xylyl, 2,4-xylyl, 2,5-ylyl, 2,6-xylyl, 3,4-xylyl, 2,4,6-trimethylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-fluorophenyl, 3-fluorophenyl, 4-fluorophenyl, 2,3-difluorophenyl, 2,4-difluorophenyl, 2,5-difluorophenyl, 2,6-difluorophenyl 2,3,5,6-tetrafluoro-3-cyanophenyl, 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 2-trifluoromethoxyphenyl, 3-trifluoromethoxyphenyl, 4-trifluoromethoxyphenyl, aminocarboxyphenyl, aminosulfonylphenyl.

Illustrative examples of $NR^6R^7$ groups of formulas I, and III above, include, but are not limited to, N-cyclopropylmethyl-N-propylamino, piperazyl, piperidyl, pirimidyl, morpholyl, thiomorpholyl, oxazinanyl and thiazinanyl.

A "subject" includes mammals, e.g., humans, companion animals (e.g., dogs, cats, and the like), farm animals (e.g., cows, sheep, pigs, horses, and the like) and laboratory animals (e.g., rats, mice, guinea pigs, and the like). In a preferred embodiment of the disclosed method, the subject is human. A subject in need of treatment is suffering from a disease or condition, the symptoms of which may be alleviated by inhibiting T-cell proliferation. Typically, a subject will be treated for a disease that is caused, at least in part, by or involves T-cell proliferation. Alternatively, the method is used to improve symptoms in a subject suffering from IBD, EAE, sepsis, rheumatoid arthritis or lupus. Preferably, the method is used to treat a subject that has IBD or sepsis The compounds may be administered to a mammal in need of treatment by any route, such as oral, pulmonary, rectal, transdermal, subcutaneous, intravenous, intramuscular, intracranial, intraperitoneal and intranasal in combination with an acceptable pharmaceutical carrier, for tableting, solubilizing, or suspending in emulsion form or for delivering by slow release from a polymeric matrix. These carriers are well known in the art, however suitable carriers for the compounds of this invention are described below.

An "effective amount" of a compound of the disclosed invention is the quantity which, when administered to a subject in need of treatment, improves the prognosis of the subject, e.g., delays the onset of and/or reduces the severity of one or more of the subject's symptoms. The amount of the disclosed compound to be administered to a subject will depend on the particular disease, the mode of administration, and the characteristics of the subject, such as general health, other diseases, age, sex, genotype, body weight and tolerance to drugs. The skilled artisan will be able to determine appropriate dosages depending on these and other factors. Effective amounts of the disclosed compounds typically range between about 0.01 mg/kg per day and about 100 mg/kg per day, and preferably between 0.1 mg/kg per day and about 10 mg/kg/day.

Preferably disclosed compounds or pharmaceutical formulations containing these compounds are in unit dosage form for administration to a subject. The unit dosage form can be any unit dosage form known in the art including, for example, a capsule, an I.V. bag, a tablet, a single pump on an aerosol inhaler, or a vial. The quantity of active ingredient (i.e., a compound of structural formula I or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes as outlined above.

A "pharmaceutically acceptable salt" of the disclosed compound can be used in the disclosed methods. For example, an acid salt of a compound containing an amine or other basic group can be obtained by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

For oral administration, the disclosed compounds or salts thereof can be combined with a suitable solid or liquid carrier or diluent to form capsules, tablets, pills, suppositories, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like.

For parenteral administration of the disclosed compounds, or salts thereof, can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition to the formulations described previously, the compounds may also be formulated as a depot preparation. Suitable formulations of this type include biocompatible and biodegradable polymeric hydrogel formulations using crosslinked or water insoluble formulations of polysaccharides, polyethylene oxides, polyacrylates, and the like. Such long acting formulations may be administered by implantation, for example, subcutaneously or intramuscularly or by intramuscular injection. Preferably, they are implanted in the microenvironment of an affected organ or tissue. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

In addition to the formulations described previously, the compounds may also be formulated as a topical preparation. Suitable formulations of this type include biocompatible oil, wax, gel, powder, polymer, or other liquid or solid carriers. Such formulations may be administered by applying directly to affected tissues. The compounds may also be formulated as suppositories. Suitable formulations include biocompatible wax.

Preferred embodiments of the compounds of this inventions are outlined in the following tables with their in-vitro assay results assessing T-cell response.

TABLE 1

1-Ethyl-3-Substituted Ureas
Formula (II): Et—NH—CO—NH—Q—R$^2$

| Comp. # | Structure | Thymidine Uptake (% Reduction @ 1 mM) |
|---|---|---|
| 2 | Et-NH-C(O)-NH-CH$_2$-(2-furyl) | 16 |
| 3 | Et-NH-C(O)-NH-CH$_2$-(tetrahydrofuran-2-yl) | 26 |

TABLE 1-continued

1-Ethyl-3-Substituted Ureas
Formula (II): Et—NH—CO—NH—Q—R²

| Comp. # | Structure | Thymidine Uptake (% Reduction @ 1 mM) |
|---|---|---|
| 4 | EtNH-CO-NH-CH₂-CH(Ph)₂ | 26 |
| 5 | EtNH-CO-NH-CH₂CH₂-(3-Cl-C₆H₄) | 24 |
| 6 | EtNH-CO-NH-CH₂CH₂-piperidinyl | 33 |
| 7 | EtNH-CO-NH-(benzo[1,2,5]thiadiazol-4-yl) | 25 |
| 8 | EtNH-CO-NH-(benzothiazol-2-yl) | 22 |
| 9 | EtNH-CO-NH-N(pyrrolidinyl) | 16 |
| 10 | EtNH-CO-NH-(3-OCF₃-C₆H₄) | 30 |
| 11 | EtNH-CO-NH-(1H-pyrazol-3-yl) | 35 |
| 12 | EtNH-CO-NH-C(CH₃)₂CH₂C(O)CH₃ | 35 |
| 13 | EtNH-CO-NH-(1-CO₂CH₂CH₃-piperidin-4-yl) | 35 |

TABLE 1-continued

1-Ethyl-3-Substituted Ureas
Formula (II): Et-NH—CO—NH—Q—R²

| Comp. # | Structure | Thymidine Uptake (% Reduction @ 1 mM) |
|---|---|---|
| 14 | *3-sulfamoylphenyl ethylurea* | 18 |
| 15 | *2,3,5,6-tetrafluoro-4-cyanophenyl ethylurea* | 26 |
| 16 | *4-carbamoylphenyl ethylurea* | 27 |
| 17 | *ethyl-[3-(propylamino)propyl]urea* | 25 |
| 18 | *O-tert-butyl N-ethylhydroxyurea* | 25 |
| 19 | *(5,6-dimethyl-1H-benzimidazol-2-yl) ethylurea* | 77 |
| 20 | *pyrazin-2-yl ethylurea* | 55 |
| 21 | *(1H-pyrazolo[3,4-d]pyrimidin-4-yl) ethylurea* | 95 |
| 22 | *(4H-1,2,4-triazol-4-yl) ethylurea* | 19 |
| 23 | *diethyl 2-(3-ethylureido)malonate* | 12 |

TABLE 1-continued
1-Ethyl-3-Substituted Ureas
Formula (II): Et-NH—CO—NH—Q—R²
| Comp. # | Structure | Thymidine Uptake (% Reduction @ 1 mM) |
|---|---|---|
| 24 | 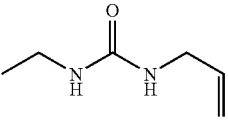 | 18 |
| 25 | 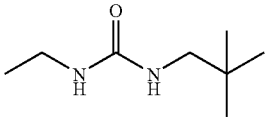 | 60 |
TABLE 2
1-Ethyl-3-(3'-Substituted-propyl)-Ureas
Formula (III): Et-NH—CO—NH—(CH₂)₃—NR⁶R⁷
| Comp. # | Structure | Thymidine Uptake (% Reduction @ 1 mM) |
|---|---|---|
| 26 | 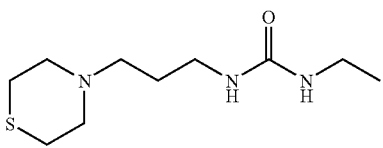 | 16 |
| 27 | 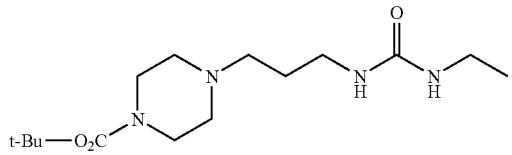 | 21 |
| 28 | 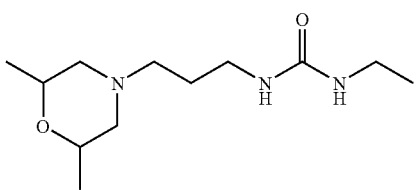 | 13 |
| 29 | 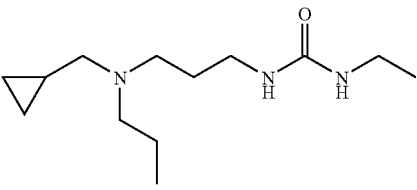 | 23 |
| 30 | 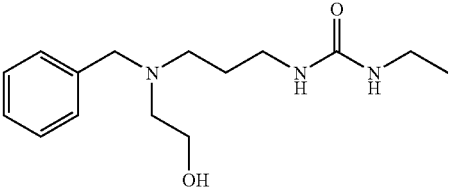 | 12 |

TABLE 2-continued
1-Ethyl-3-(3'-Substituted-propyl)-Ureas
Formula (III): Et-NH—CO—NH—(CH$_2$)$_3$—NR$^6$R$^7$
| Comp. # | Structure | Thymidine Uptake (% Reduction @ 1 mM) |
|---|---|---|
| 31 | 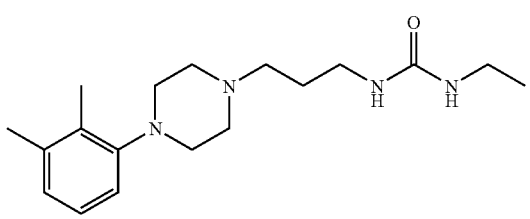 | 21 |
| 32 | 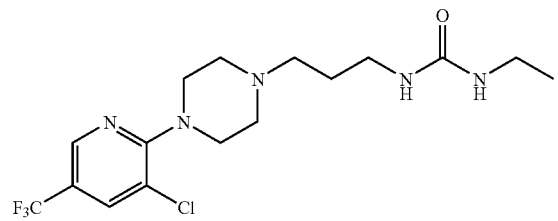 | 27 |
| 33 | 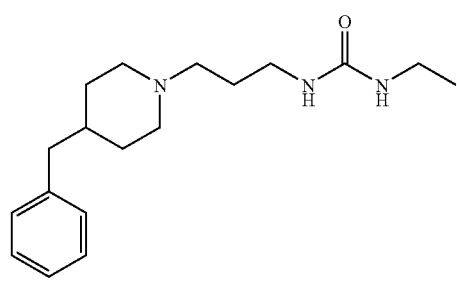 | 17 |
| 34 | 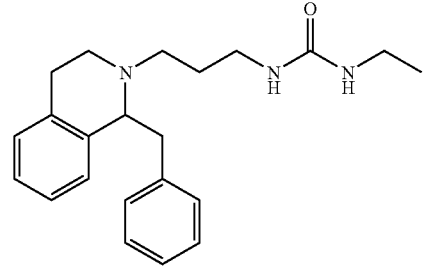 | 12 |
| 35 | 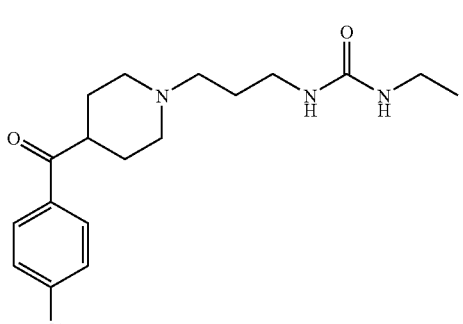 | 55 |

TABLE 2-continued

1-Ethyl-3-(3'-Substituted-propyl)-Ureas
Formula (III): Et-NH—CO—NH—(CH$_2$)$_3$—NR$^6$R$^7$

| Comp. # | Structure | Thymidine Uptake (% Reduction @ 1 mM) |
|---|---|---|
| 36 | 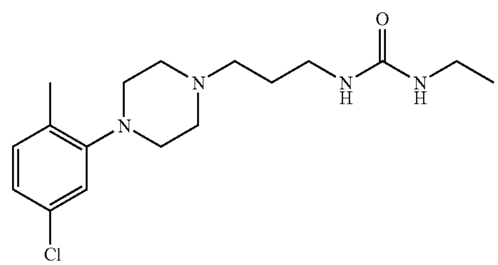 | 18 |
| 37 | 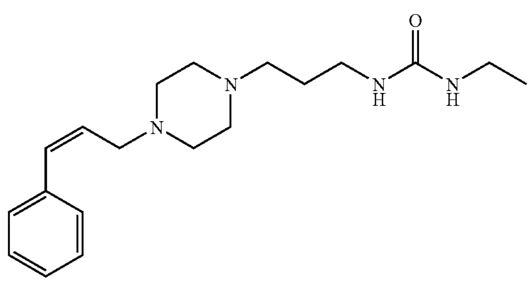 | 23 |
| 38 | 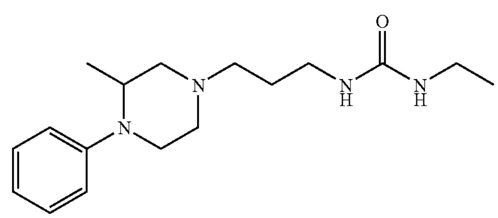 | 13 |
| 39 | 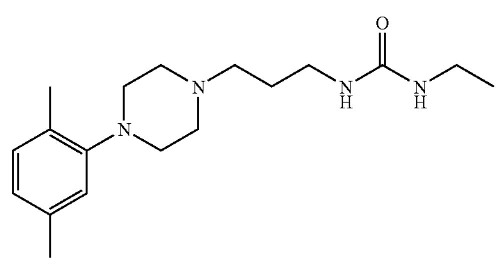 | 23 |

TABLE 3

1-(3'-Dimethylaminopropyl)-3-Substituted-Ureas
Formula (IV): Me$_2$N—(CH$_2$)$_3$—NH—CO—NH—Q—R$^2$

| Comp # | Structure | Thymidine Uptake (% Reduction @ 1 mM) |
|---|---|---|
| 40 | 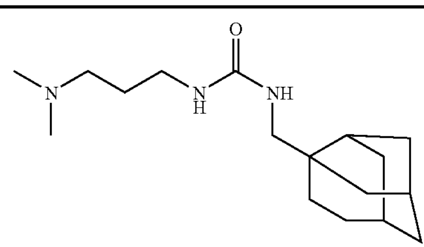 | 20 |

TABLE 3-continued
1-(3'-Dimethylaminopropyl)-3-Substituted-Ureas
Formula (IV): Me$_2$N—(CH$_2$)$_3$—NH—CO—NH—Q—R$^2$
| Comp # | Structure | Thymidine Uptake (% Reduction @ 1 mM) |
|---|---|---|
| 41 | 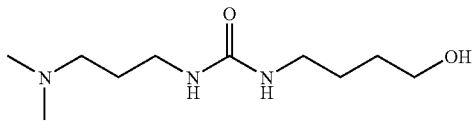 | 12 |
| 42 | 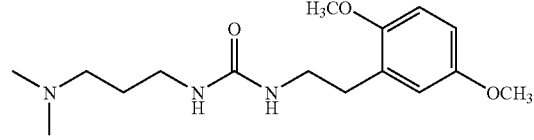 | 31 |
| 43 | 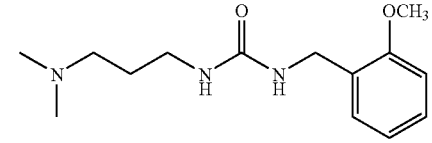 | 24 |
| 44 | 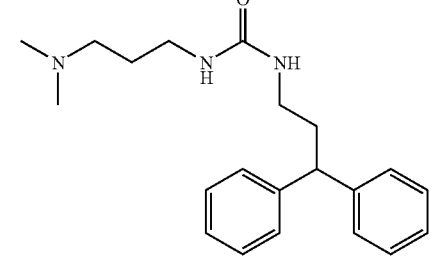 | 21 |
| 45 | 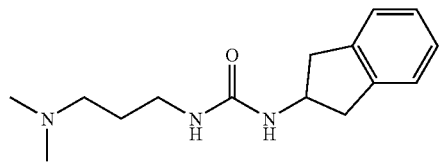 | 20 |
| 46 | 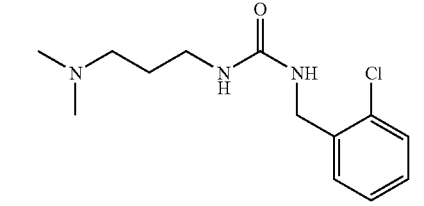 | 21 |
| 47 | 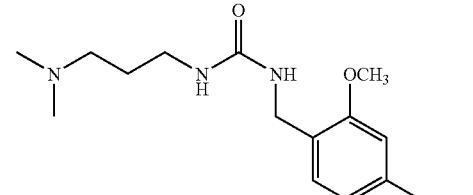 | 20 |
| 48 | 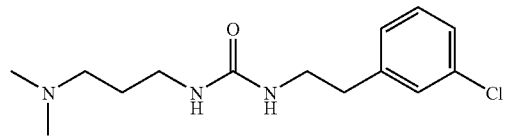 | 26 |

TABLE 3-continued
1-(3'-Dimethylaminopropyl)-3-Substituted-Ureas
Formula (IV): Me$_2$N—(CH$_2$)$_3$—NH—CO—NH—Q—R$^2$
| Comp # | Structure | Thymidine Uptake (% Reduction @ 1 mM) |
|---|---|---|
| 49 | 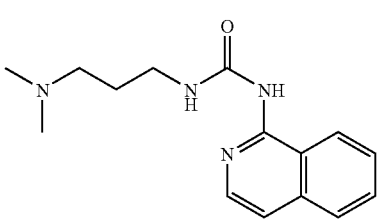 | 36 |
| 50 | 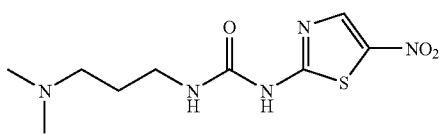 | 22 |
| 51 | 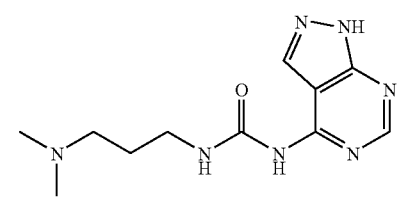 | 86 |
| 52 | 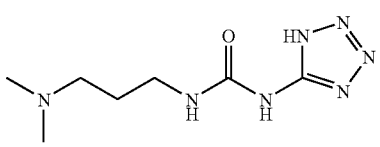 | 14 |
| 53 | 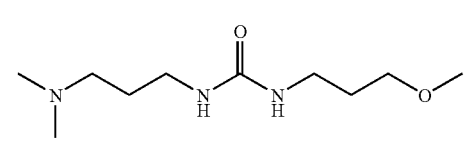 | 26 |
| 54 | 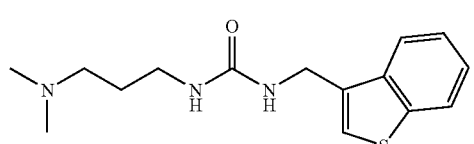 | 16 |
| 55 | 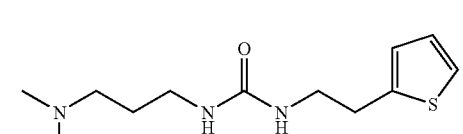 | 17 |

TABLE 4

Salts of Substituted Ureas

| Comp. # | Free Base | Salt Form |
|---|---|---|
| 56 | 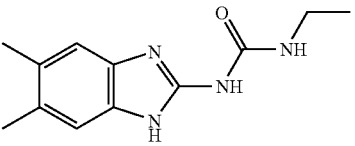 | HCl |
| 57 | 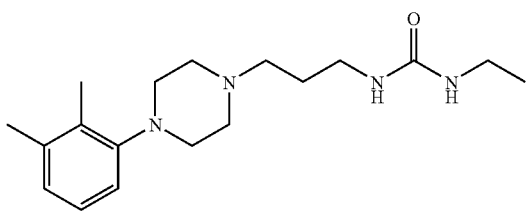 | Fumarate |
| 58 | 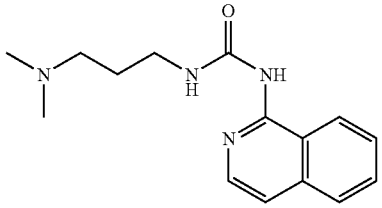 | Fumarate |

EXAMPLES

Example 1

General Synthetic Method 1

(Compound in Table 1)

$$\text{Et-NC}+R^2\text{Q-NH}_2 \rightarrow \text{Et-NH—CO—NH-Q-}R^2 \quad \text{(II)}$$

To a stirred solution of amine ($R^2$Q-NH$_2$) in methylene chloride is added a solution of ethyl isocyanate (1.1 equivalents) in methylene chloride. The reaction is allow to stir at room temperature overnight. The reaction is concentration in-vacuo and the residue is dissolved in ethyl acetate. It is then washed successively with aqueous 1 N hydrochloric acid, aqueous saturated sodium bicarbonate solution, brine, dried over sodium sulfate and concentrated.

Example 2

General Synthetic Method 2

(Compound in Table 2)

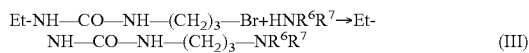
$$\text{Et-NH—CO—NH—(CH}_2)_3\text{—Br}+\text{HNR}^6R^7 \rightarrow \text{Et-NH—CO—NH—(CH}_2)_3\text{—NR}^6R^7 \quad \text{(III)}$$

To a stirred solution of 1-(3'-bromopropyl)-3-ethyl urea in acetonitrile is added potassium carbonate (2.1 equivalents) and a secondary amine. The reaction is heated to reflux and allowed to stir overnight. The reaction is cooled to room temperature and partitioned between ethyl acetate and water. The organic layer is separated and washed with brine, dried over sodium sulfate and concentrated.

Example 3

General Synthetic Method 3

(Compounds in Table 3)

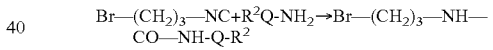
$$\text{Br—(CH}_2)_3\text{—NC}+R^2\text{Q-NH}_2 \rightarrow \text{Br—(CH}_2)_3\text{—NH—CO—NH-Q-}R^2$$

Step 1: To a stirred solution of amine dissolved in methylene chloride at room temperature is added dropwise 3-bromopropyl isocyanate dissolved in methylene chloride. The reaction is allowed to stir overnight. The reaction was partitioned between methylene chloride and aqueous saturated sodium bicarbonate. The organic layer is separated, washed with brine, dried over sodium sulfate and concentrated.

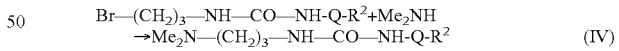
$$\text{Br—(CH}_2)_3\text{—NH—CO—NH-Q-}R^2+\text{Me}_2\text{NH} \rightarrow \text{Me}_2\text{N—(CH}_2)_3\text{—NH—CO—NH-Q-}R^2 \quad \text{(IV)}$$

Step 2: The product from Step 1 is dissolved in excess 2.0M dimethylamine in tetrahydrofuran. The reaction is warmed to 45° C. and let stir overnight. The reaction is concentrated and partitioned between methylene chloride and aqueous saturated sodium bicarbonate. The organic layer is separated, washed with brine, dried over sodium sulfate and concentrated.

Example 4

Synthesis of Compound No. 19

(Compound in Table 1)

To a stirred solution of 2-amino-5,6-dimethylbenzimidazole (484 mg, 3.0 mmol) in methylene chloride (10 ml) was added dropwise a solution of ethyl isocyanate (220 mg, 3.3 mmol) in methylene chloride (1 ml). The reaction was allowed to stir at room temperature overnight. The reaction was concentrated in-vacuo and the residue was dissolved in ethyl acetate (20 ml). It was then washed successively with aqueous 1N hydrochloric acid, aqueous saturated sodium bicarbonate, brine, dried over sodium sulfate and concentrated. The resulting solid was recrystallized from methanol/water to give 471 mg (68%) of a tan solid. $^1$H NMR (CDCl$_3$) δ 7.08 (s, 1H), 7.02 (s, 1H), 3.47 (q, 2H), 2.24 (s, 3H), 2.22 (s, 3H), 1.30 (t, 3H) ppm.

Example 5

Synthesis of Compound No. 56

(Hydrochloride Salt of Compound No. 19)

To a stirred solution of 1-(5,6-dimethyl-1H-benzoimidazol-2-yl)-3-ethyl urea (1.46 g, 6.3 mmol) in acetone (30 ml) was bubbled in hydrogen chloride gas. A precipitate formed which was collected by filtration, washed with acetone and dried in a vacuum oven to give 1.35 g (80%) of an off-white solid. $^1$H NMR (D$_2$O ) □ 6.88 (s, 1H), 6.82 (s, 1H), 3.24 (q, 2H), 2.07 (s, 6H), 1.07 (t, 3H) ppm.

Example 6

Synthesis of Compound No. 31

(Compound in Table 2)

To a stirred solution of 1-(3'-bromopropyl)-3-ethyl urea (2.1 g, 10 mmol), see below, in acetonitrile (25 ml) was added potassium carbonate (2.9 g, 21 mmol) and 1-(2,3-xylyl)piperazine hydrochloride (2.27 g, 10 mmol). The reaction was heated to reflux and allowed to stir overnight. The reaction was cooled to room temperature and partitioned between ethyl acetate (40 ml) and water (30 ml). The organic layer was separated and washed with brine, dried over sodium sulfate and concentrated. Flash chromatography over silica gel (10:1 methylene chloride/2M ammonia in methanol) gave 1.21 g (38%) of an off white solid. $^1$H NMR (CDCl$_3$) δ 7.08 (t, 1H), 6.91 (dd, 2H), 5.31 (bs, 1H), 4.98 (bs, 1H), 3.28 (t, 2H), 3.21 (m, 2H), 2.91 (bs, 4H), 2.65 (bs, 4H), 2.54 (t, 2H) 2.26 (s, 3H), 2.21 (s, 3H), 1.72 (m, 2H), 1.14 (t, 3H) ppm.

Example 7

Synthesis of 1-(3'-bromopropyl)-3-ethyl urea (Precursor to Compound No. 31)

To a stirred solution of 3-bromopropylamine hydrobromide (10.0 g, 45.7 mmol) in methylene chloride (100 ml) containing triethylamine (5.08 g, 50.2 mmol) was added ethyl isocyanate (3.24 g, 45.7 mmol) in methylene chloride (10 ml). Let stir at room temperature for 3 hours. The reaction was poured into aqueous 1N hydrochloric acid. The organic layer was separated and washed with brine, dried over sodium sulfate and concentrated to give 6.66 g (70%) of a white solid. $^1$H NMR (CDCl$_3$) δ 3.41 (t, 2H), 3.29 (t, 2H), 3.20 (q, 2H), 2.05 (m, 2H), 1.14 (t, 3H) ppm.

Example 8

Synthesis of Compound No. 57

(Fumarate Salt of Compound No. 31)

To a stirred solution of 1-{3'-[4-(2,3-xylyl)-piperazin-1-yl]-propyl}-3-ethyl urea (933 mg, 2.93 mmol) in acetone (15 ml)/methylene chloride (5 ml) was added fumaric acid (340 mg, 2.93 mmol) in acetone (30 ml) dropwise over 2 minutes. A precipitate formed which was collected by filtration, washed with acetone and dried in a vacuum oven to give 1.09 g (98%) of a white solid. $^1$H NMR (D$_2$O) δ 6.99 (t, 1H), 6.84 (m, 2H), 6.47 (s, 1H), 3.45 (bd, 2H), 3.89 (m, 8H) 2.93 (q, 2H), 2.87 (m, 2H), 2.07 (s, 3H), 2.01 (s, 3H), 0.88 (t, 3H) ppm.

Example 9

Synthesis of Compound No. 42

(Compound in Table 3)

Step 1: To a stirred solution of 1-aminoisoquinoline (2.5 g, 17.3 mmol) in methylene chloride (50 ml) was added 3-bromopropyl isocyanate (3.13 g, 19 mmol) dissolved in methylene chloride (15 ml). The mixture was allowed to stir at room temperature overnight. The mixture was partitioned between methylene chloride (20 ml) and aqueous saturated sodium bicarbonate (20 ml). The organic layer was separated and washed with brine, dried over sodium sulfate and concentrated to give 4.97 g of a brown solid (92%). This was used directly in the next step.

Step 2: The 1-(3'-bromopropyl)-3-isoquinolin-1-yl urea from step 1 was dissolved in excess 2M dimethylamine in tetrahydrofuran (10 ml) in a sealed tube. Warmed to 50° C. and let stir overnight. The reaction mixture was partitioned between diethyl ether (75 ml) and aqueous saturated sodium bicarbonate (25 ml). The organic layer was separated and washed with brine, dried over sodium sulfate and concentrated. Flash chromatography over silica gel (10:1 methylene chloride/2M ammonia in methanol) provided 3.12 g (70%) of an off-white solid. $^1$H NMR (CDCl$_3$) δ 10.24 (bs, 1H), 8.48 (bs,1H), 8.20 (d, 1H), 8.03 (d,1H), 7.75 (d, 1H), 7.69 (t,1H), 7.60 (t,1H), 7.23 (d,1H), 3.52 (q, 2H), 2.43 (t, 2H), 2.28 (s, 6H), 1.87 (t, 2H) ppm.

Example 10

Synthesis of Compound 58

(Fumarate Salt of Compound No. 49)

The 1-(3'-dimethylaminopropyl)-3-isoquinolin-1-yl urea (417 mg, 1.53 mmol) from step 2 was dissolved in acetone (10 ml). With stirring, fumaric acid (180 mg, 1.55 mmol) dissolved in acetone (35 ml) was added dropwise over 2 minutes. A precipitate formed which was collected by filtration, washed with acetone and dried in a vacuum oven to give 260 mg (51%) of a white solid. $^1$H NMR (D$_2$O) δ 8.91 (bd,1H), 7.82 (bs,1H), 7.67 (d,1H), 7.58 (t,1H), 7.47 (t,1H) 7.24 (bs, 1H), 6.31 (s, 1H), 3.24 (t, 2H), 3.04 (t, 2H), 2.71 (s, 6H), 1.85 (m, 2H) ppm.

Example 11

Cytokine Inhibition with compound No. 56

TABLE 5

| Cellular Assay | Conc. | Criteria | % Inhibition | IC$_{50}$ |
| --- | --- | --- | --- | --- |
| Mediator Release, IL-1β | 10 mM | ≧±50% | 91% | 2.06 μM |
| Mediator Release, IL-10 | 10 mM | ≧±50% | 63% | 5.74 μM |
| Mediator Release, IL-5 | 10 mM | ≧±50% | 54% | 9.28 μM |
| Mediator Release, IL-6 | 10 mM | ≧±50% | 82% | 3.89 μM |
| Mediator Release, Interferon-γ | 10 mM | ≧±50% | 57% | 6.49 μM |

TABLE 5-continued

| Cellular Assay | Conc. | Criteria | % Inhibition | IC$_{50}$ |
|---|---|---|---|---|
| Mediator Release, TNF-α | 10 mM | ≧±50% | 89% | 1.94 μM |
| Transcription Response, NF-κB | 10 mM | ≧±50% | 52% | 9.65 μM |

Example 12

Inflammatory Bowel Disease

CM Hogaboam et al., Eur. J. Pharmacol.; 309; 261 (1996)

Groups of 3 derived-male, overnight-fasted rats weighing 150±10 g are used. Distal colitis is induced by intra-colonic instillation of 0.5 ml/rat of DNBS (2,4-dinitrobenzene sulfonic acid, 60 mg/ml in ethanol 30%) after which air (2 ml) is gently injected through the cannula to ensure that the solution remains in the colon. Test compound is administered orally 24 and 2 hours before DNBS instillation and then daily for 5 days in total of 7 doses. The animals are sacrificed 24 hours after the final dose of test compound administration and each colon is removed and weighed. A 30 percent or more (≧30%) inhibition in net increase of colon to 100 g body weight ratio, relative to vehicle-control-2 group is considered significant.

Compound no. 56 showed dose responsive activity and statistically significant response at the highest dose (25 mg/kg).

| Treatment | Dose (PO) | Ave. | Net Inc. | Inhibition |
|---|---|---|---|---|
| Vehicle (10% Cremophor/ 10% Ethanol) (No DNBS administration) | 10 ml/kg × 7 | 0.297 | — | — |
| Vehicle (10% Cremophor/ 10% Ethanol) (With DNBS administration) | 10 ml/kg × 7 | 0.731 | 0.434 | — |
| Compound no. 56 | 25 mg/kg × 7 | 0.585 | 0.288 | 34 |
|  | 5 mg/kg × 7 | 0.678 | 0.381 | 12 |
| Sulfasalazine | 300 mg/kg × 7 | 0.551 | 0.254 | 41 |

Example 13

Septic Shock, Lipopolysaccharide

K M Mohler et al., Nature; 370; 218 (1994).

Groups of 4 or 6 C57/BL mice weighing 18–20g were used. Test substance at a dose of 25 and 5 mg/kg (10% cremophor/10% ethanol) is administered IP one hour before challenge with lipopolysaccharide (LPS, from *E. coli*, LD100 of 20 ng/animal IV) plus galactosamine (20 mg/animal IV). The blank control group was only applied 10% cremophor/10% ethanol IP and without LPS challenge. Mortality is recorded every 12 hours after challenge over a 3-day period. Protection of mortality by 50 percent or more (≧50%) indicates significant activity.

Compound no. 56 showed dose responsive activity and statistically significant response at the highest dose (25 mg/kg).

| Treatment | Dose (IP) | N | Total Deaths | Inhibition |
|---|---|---|---|---|
| Vehicle (10% Cremophor/ 10% Ethanol) (No DNBS administration) | 10 ml/kg | 4 | 0 | — |
| Vehicle (10% Cremophor/ 10% Ethanol) (With DNBS administration) | 10 ml/kg | 4 | 4 | — |
| Compound no. 56 | 25 mg/kg | 6 | 3 | 50 |
|  | 5 mg/kg | 6 | 5 | 17 |
| Dexamethasone-21-acetate (PO dose) | 1 mg/kg | 4 | 0 | 100 |

Example 14

Autoimmune Encephalomyelitis (EAE) Model Ref

The purpose of this study was to test the efficacy of several different small molecule compounds. Forty-eight female SJL/J mice, 8 weeks in age, were divided into nine test groups. Mice were immunized with proteolipid protein peptide (PLP) 139–151 (50 μg/mouse) dissolved in PBS and emulsified with an equal volume of Complete Freund's Adjuvent, supplemented with 4 mg/ml Mycobacterium tuberculosis H37Ra, by injecting 100 μl s.c. in the lower abdominal area at two sites. Each mouse also received an injection of pertussis toxin (100 ng) into the tail vein immediately following immunization and again 48 hours later. The PLP 139–151 was supplied by Dr. Vijay Kuchroo, Center of Neurological Diseases, Brigham & Women's Hospital, Boston, Mass.

The animals were injected IP or PO daily with either compound or vehicle from day 1 to day 16. At the first sign of disease (day 9), each animal was assessed daily and given a disease severity score (ADSS) between 0 (no disease) and 5 (moribund or dead).

Figure 2:
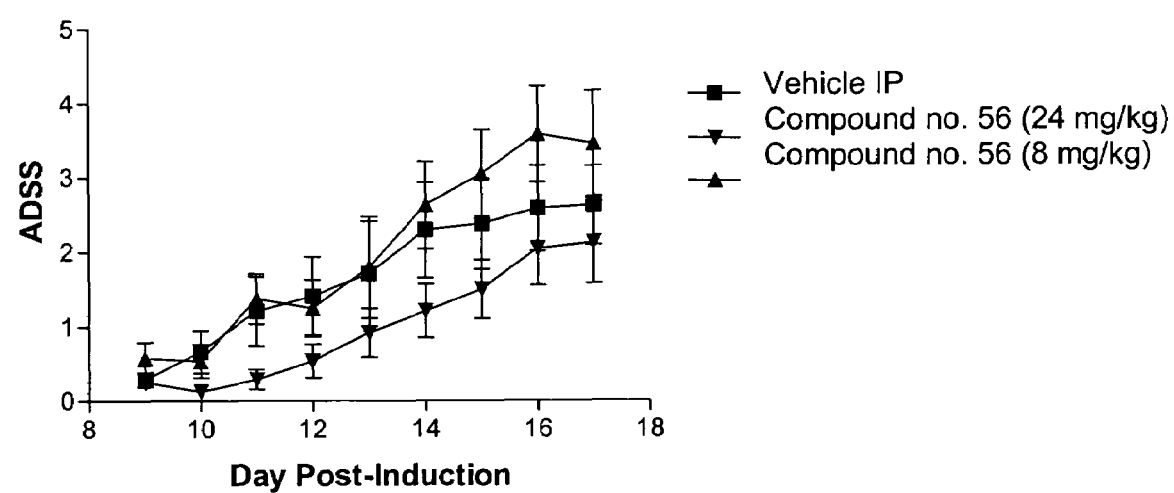
FIG. 2 is a plot of the assessment of the disease severity score (ADSS) over time post challenge in a mouse model of EAE for control (vehicle) and treated with a compound of the invention at two doses.

Compound no. 56 dosed at 24 mg/kg had a significant effect on both disease onset and disease severity, as shown in FIG. 2. Compound no. 57 dosed at 25 mg/kg had an effect on disease onset, but not on maximum severity, as shown in FIG. 1.

We claim:

1. A compound of formula I:

R$^1$—NH—CO—NH-Q-R$^2$   (I)

or a pharmaceutically acceptable salt thereof
wherein
R$^1$ s a lower C2–C5 alkyl group, straight or branched chain and optionally substituted by an amino group of formula —NR$^3$R$^4$, wherein R$^3$ and R$^4$ are independently H, or C1–C3 alkyl group;
Q is either a bond or a divalent C1–C5 straight or branched alkyl or aikenyl group;
R$^2$ is one of the following groups
a. C5–C10 heteroaryl group selected from furanyl, pyrrolyl, pyrazolyl, imidazolyl, triazolyl, dithiolyl, oxathiolyl, isoxazolyl, piridazinyl, pyrimidinyl, pyrazinyl, indolyl, isoquinolinyl, benzimidazolyl, benzoxaziyl, benzothiadiazolyl nanhthyridinyl, pyrido[3,4-b]pyridinyl, pyrido[3,2-b]b pyridinyl, pyrido[4,3-b]hyridinyl, and 4-aminopyrazolo[3,4d] pyrimidinyl
b. C5–C10 heterocyclic group selected from piperazyl, tetahydrofuranyl, dioxanyl, wherein the heteroaryl, or heterocyclic ring is unsubstituted or substituted by one or more of the following groups
  i. $R^5$, —CN, Halogen, $OR^5$, —$COR^5$, —$CO_2R^5$, $OCF_3$, —$CONH_2$, —$SO_2NH_2$, and $NO_2$, wherein $R^5$ is a C1 to C4 straight or branched alkyl group, and
c. $N^6R^7$, wherein $R^6$ and $R^7$ are
  together with the N forming a 5 or 6 membered monocyclic ring having one or more ring positions occupied by another N, S, or O, wherein the heteroaryl ring thus formed is unsubstituted or substituted by one or more of the following groups
    1. $R^5$, —CN, halogen, $OR^5$, —$COR^5$, —$CO_2R^5$, $OCF_3$, —$CONH_2$, —$SO_2NH_2$,
    2. C1–C5 aikyl or alkylene group substituted by an aryl group, and
    3. C6 or C10 aryl or heteroaryl group unsubstituted or substituted by one ore more of $R^5$, $CF_3$, and halogen, wherein the aryl or hetero aryl may be a pending group off one position of, or a fused with, the $NR^6R^7$ ring.

2. The compound of claim 1 wherein $R^1$ is ethyl.

3. The cormpound of claim 1 wherein $R^1$ is dimethylaminopropyl.

4. The compound of claim 1 having Formula (III): Et-NH—OC—NH—$(CH_2)_3$—$NR^6R^7$.

5. The compound of claim 1 having the structure of

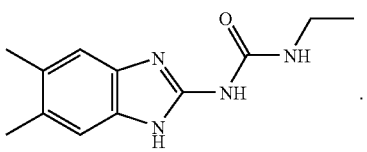

6. The compound of claim 1 having the structure of

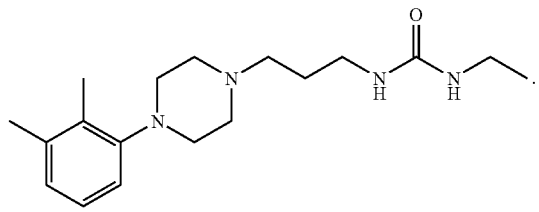

7. The compound of claim 1 having the structure of

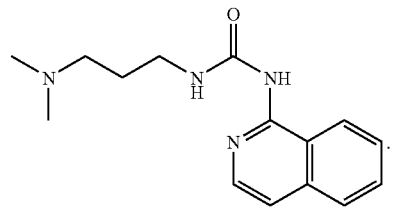

8. A method of treating an inflammatory cond Won or disease by administering an effective amount of a compound of any one of the preceding claim in a pharmaceutically acceptable carrier.

9. The method of claim 8, wherein the condition is inflammatory bowel disease, autoimmune encephalomyelitis, lupus, or sepsis.

10. The method of claim 8, wherein the carrier is buffered saline.

* * * * *